United States Patent [19]
Hektner

[11] Patent Number: 5,944,716
[45] Date of Patent: Aug. 31, 1999

[54] RADIO FREQUENCY TRANSMYOCARDIAL REVASCULARIZATION CORER

[75] Inventor: Thomas R. Hektner, Medina, Minn.

[73] Assignee: SciMed Life Systems, Inc., Maple Grove, Minn.

[21] Appl. No.: 08/792,094

[22] Filed: Jan. 31, 1997

Related U.S. Application Data

[60] Provisional application No. 60/032,804, Dec. 9, 1996.

[51] Int. Cl.$^6$ .................................................. A61B 17/39
[52] U.S. Cl. ........................ 606/45; 606/41; 606/46; 607/101
[58] Field of Search .......................... 606/28, 34, 37, 606/41, 45, 46; 600/373, 374; 607/119, 122, 101, 102

[56] References Cited

U.S. PATENT DOCUMENTS

| | | | |
|---|---|---|---|
| 4,790,311 | 12/1988 | Ruiz | 128/303.1 |
| 4,896,671 | 1/1990 | Cunningham et al. | 128/642 |
| 5,047,026 | 9/1991 | Rydell | 606/48 |
| 5,093,877 | 3/1992 | Aita et al. | 385/34 |
| 5,358,485 | 10/1994 | Vance et al. | 604/22 |
| 5,364,393 | 11/1994 | Auth et al. | 606/34 |
| 5,370,675 | 12/1994 | Edwards et al. | 606/32 |
| 5,380,316 | 1/1995 | Aita et al. | 606/7 |
| 5,389,096 | 2/1995 | Aita et al. | 606/15 |
| 5,403,311 | 4/1995 | Abele et al. | 606/45 |
| 5,522,815 | 6/1996 | Durgin, Jr. et al. | 606/50 |
| 5,591,159 | 1/1997 | Taheri | 606/15 |
| 5,593,405 | 1/1997 | Osypka | 606/15 |
| 5,607,405 | 3/1997 | Decker et al. | 604/264 |
| 5,620,414 | 4/1997 | Campbell, Jr. | 604/22 |
| 5,672,174 | 9/1997 | Gough et al. | 606/41 |
| 5,681,308 | 10/1997 | Edwards et al. | 606/41 |
| 5,683,366 | 11/1997 | Eggers et al. | 604/114 |
| 5,697,882 | 12/1997 | Eggers et al. | 604/114 |
| 5,700,259 | 12/1997 | Negus et al. | 606/14 |
| 5,713,894 | 2/1998 | Murphy-Chutorian et al. | 606/15 |
| 5,725,521 | 3/1998 | Mueller | 606/7 |
| 5,725,523 | 3/1998 | Mueller | 606/15 |

FOREIGN PATENT DOCUMENTS

| | | |
|---|---|---|
| 296 09 350 U1 | 10/1996 | Germany. |
| 195 37 084 A1 | 4/1997 | Germany. |
| WO 96/35469 | 11/1996 | WIPO. |
| WO 97/18768 | 5/1997 | WIPO. |
| WO 97/29803 | 8/1997 | WIPO. |
| WO 97/32551 | 9/1997 | WIPO. |
| WO 97/44071 | 11/1997 | WIPO. |
| WO 96/39963 | 12/1997 | WIPO. |

OTHER PUBLICATIONS

M. L. Goldman et al., "Nonoperative Portacaval Shunt in Swine," *Investigative Radiology*, vol. 25, No. 5, May 1990, pp. 574–578.

Abstract entitled "Transventricular Revascularization by Laser", *Lasers in Surgery and Medicine*, 1982, 1 page.

Abstract entitled "Analysis of Photoproducts, Free Radicals and Particulate Debris Generated During In–Vivo Argon Laser Myoplasty", *Lasers in Surgery and Medicine*, 1991, 1 page.

Isner, J., "Right Ventricular Myocardial Infarction", *The Journal of the American Medical Association*, V259, N5, Feb. 5, 1988, 12 pages.

Abstract entitled "Proliferative Activity in Peripheral and Coronary Atherosclerotic Plaque . . . ", *J. Clin. Invest.*, Apr., 1993, 1 page.

(List continued on next page.)

*Primary Examiner*—Jack W. Lavinder
*Assistant Examiner*—David M. Ruddy
*Attorney, Agent, or Firm*—Crompton, Seager & Tufte

[57] ABSTRACT

An RF activated catheter apparatus for performing transmyocardial revascularization. The catheter apparatus including an elongate catheter shaft having proximal and distal ends, the distal end including an RF emitter which is coupled to an RF generator for cutting channels into the myocardium of a patient's heart.

4 Claims, 3 Drawing Sheets

OTHER PUBLICATIONS

A. Vineberg et al., "Creation of Intramyocardial Pathways to Channel Oxygenated Blood Between Ventricular Arteriolar Zones", *Canad. Med. Assoc. Journal*, Feb. 4, 1967, vol. 96, pp. 277–279.

A. Vineberg, M.D., "Results of 14 Years' Experience in the Surgical Treatment of Human Coronary Artery Insufficiency", *Canad. Med. Assoc. Journal*, Feb. 13, 1965, vol. 92, pp. 325–332.

A. Vineberg et al., "The Ivalon Sponge Procedure for Myocardial Revascularization", *Surgery*, vol. 47, No. 2, Feb., 1960, pp. 268–289.

A. Vineberg et al., "Investigative Surgery: Treatment of Acute Myocardial Infarction by Endocardial Resection", *Surgery*, vol. 57, No. 6, Jun., 1965, pp. 832–835.

P. Walter et al., "Treatment of Acute Myocardial Infarction by Transmural Blood Supply From the Ventricular Cavity", *Europ. Surg. Res.*, 3:130–138 (1971).

H.A. Khazei et al., "Myocardial Canalization: New Method of Myocardial Revascularization", *The Annals of Thoracic Surgery*, vol. 6, No. 2, Aug., 1968, pp. 163–171.

J. Hershey et al., "Transmyocardial Puncture Revascularization: a Possible Emergency Adjunct to Arterial Implant Surgery", *Geriatrics*, Mar., 1969, pp. 101–108.

Press Release dated Oct. 21, 1996, entitled "Doctors Demonstrate Proof of Blood Flow Through Open TMR Channels Created with PLC Systems . . . ", PLC Systems, Inc., 1 page.

Press Release dated Oct. 10, 1996, entitled "Texas Fieart Institute Presents Study Comparing the Use of CO2, Holmrum and Excimer Lasers for TMR", 1 page.

RADIO FREQUENCY TRANSMYOCARDIAL REVASCULARIZATION CORER

RELATED CASE

This application claims the benefit of U.S. Provisional Application No. 60/032,804, filed Dec. 9, 1996. The present application is related to U.S. patent application Ser. No. 08/884,058, filed Jun. 27, 1997, entitled "Radio Frequency Transmyocardial Revascularization", and is incorporated herein by reference.

FIELD OF THE INVENTION

The present invention pertains to a device and method for performing transmyocardial revascularization (TMR) using radio frequency (RF) energy.

BACKGROUND OF THE INVENTION

A number of techniques are available for treating cardiovascular disease such as cardiovascular bypass surgery, coronary angioplasty, laser angioplasty and atherectomy. These techniques are generally applied to bypass or open lesions in coronary vessels to restore or increase blood flow to the heart muscle. In some patient's the number of lesions is so great, or the location so remote in the patient's vasculature, that restoring adequate blood flow to the heart muscle is difficult.

TMR has been developed as an alternative to these techniques which are directed at bypassing or removing lesions. TMR is performed by boring channels directly into the myocardium of the heart. In one such procedure, a laser catheter is advanced into the left ventricle. Laser radiation is then focused on the myocardium to create a channel. It has been found that creating several channels may be useful.

TMR has been performed by forming channels with laser energy as described above. TMR has also been performed by cutting a channel with a sharpened probe or blade. The channels cut by laser have a width proportional to the width of the focused laser radiation used to make the channels. When a laser is used, tissue is vaporized to form the channel. When the procedure is performed with a blade, tissue is not removed, but merely pierced or cut.

Lasers used to performed TMR can be costly and the depth of the channels formed can be difficult to control. Cutting the myocardium with a blade does not remove material from the incision. Removing, or in the case of the TMR laser techniques, vaporization of tissue is believed to enhance the success of the TMR procedure.

SUMMARY OF THE INVENTION

The present invention pertains to an apparatus and method for performing TMR using RF energy. The apparatus and method of the present invention provides a means for performing TMR by creating channels in the myocardium of the patient's heart which can vary in length and width. The depth of the channels is generally believed to be directly proportional to the distance which the catheter of the present invention is advanced into the patient's myocardium.

Two theories underlie this procedure. The leading theory holds that creation of the channels causes angiogenesis as a healing response. When angiogenesis occurs, additional blood vessels grow in the myocardium near the channels. The second theory of TMR is that the creation of channels provides direct access of pooled blood in the heart to the heart muscle.

In one embodiment of the present invention, an RF activated catheter is provided for boring channels into the myocardium of a patient's heart. The RF activated catheter includes an elongate shaft having a proximal end and a distal end. A lumen extends through the shaft between the proximal and distal ends. A cutting tip is disposed at the distal end of the shaft. The cutting tip has proximal and distal ends and a lumen extending therebetween in fluid communication with the shaft lumen. A wire connects the cutting tip to an RF generator. The distal end of the tip is sharpened.

The catheter is used in a catheter assembly including an RF generator coupled to the cutting tip. A vacuum source is connected to the catheter proximate its proximal end and is in fluid communication with the catheter shaft lumen.

The catheter assembly preferably includes a second catheter having a proximal end and a distal end and a lumen extending therethrough between the ends. The first catheter can be advanced through the lumen of the second catheter. The second catheter preferably includes a balloon disposed around and at its distal end. An inflation lumen is provided through the second catheter in fluid communication with the balloon.

To perform TMR using this catheter assembly, the cutting tip is advanced to the patient's heart. This is preferably done percutaneously via the femoral artery. The RF generator is activated to deliver RF energy to the cutting tip. The cutting tip is advanced into the myocardium of the patient's heart to form channels therein. A second catheter can be disposed over the distal cutting tip to isolate the cutting tip from pooled blood within the patient's ventricle. Tissue within the cutting tip can be aspirated through the RF activated catheter.

DETAILED DESCRIPTION OF THE INVENTION

Figure 1:
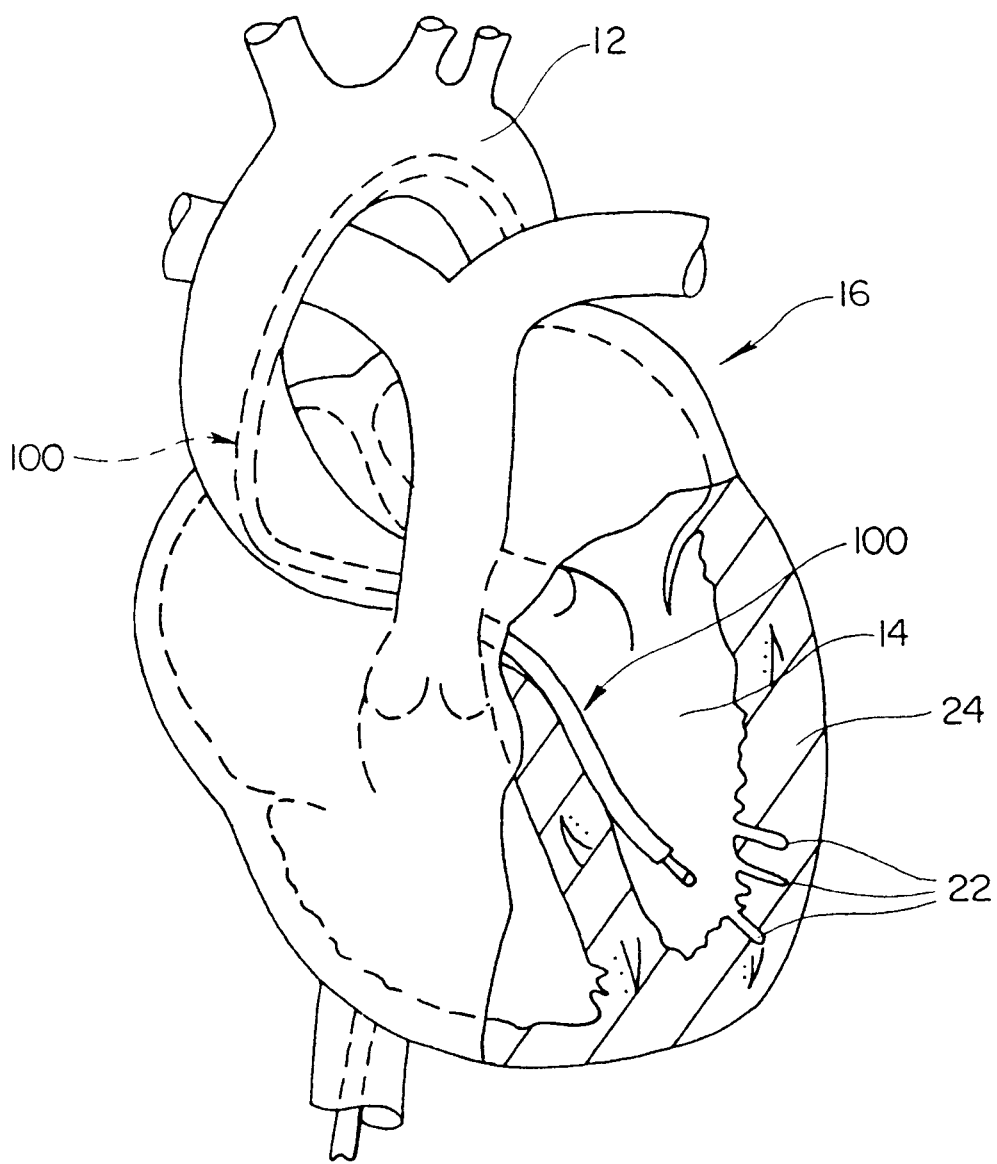
FIG. 1 is a cut-away view of a human heart including an RF transmyocardial revascularization catheter apparatus in accordance with the present invention.

Referring now to the drawings wherein like reference numerals represent like elements throughout the several views, FIG. 1 is a view of a portion of an radio frequency transmyocardial revascularization (RF TMR) catheter assembly 100 disposed within an aorta 12 and a left ventricle 14 of a heart 16. The elements of catheter assembly shown in FIG. 1 include an RF activated catheter 118, partially extending from a tubular catheter 120. Catheter 118 can be deflectable or steerable with wires (not shown). Catheter 120 can be a guide catheter, deflectable tip catheter or the like, for advancing RF activated catheter 118 therethrough or to shield portions of a patient's anatomy from RF energy emitted from catheter 118. Three channels 22 cut by catheter 118 are shown in myocardium 24 of heart 16. As a consequence of creating these channels by performing the TMR procedure, it is believed that revascularization of the myocardium near the channels occurs by angiogenesis, the channels themselves provide access by pooled blood from ventricle 14 to myocardial tissue or both.

Figure 2:
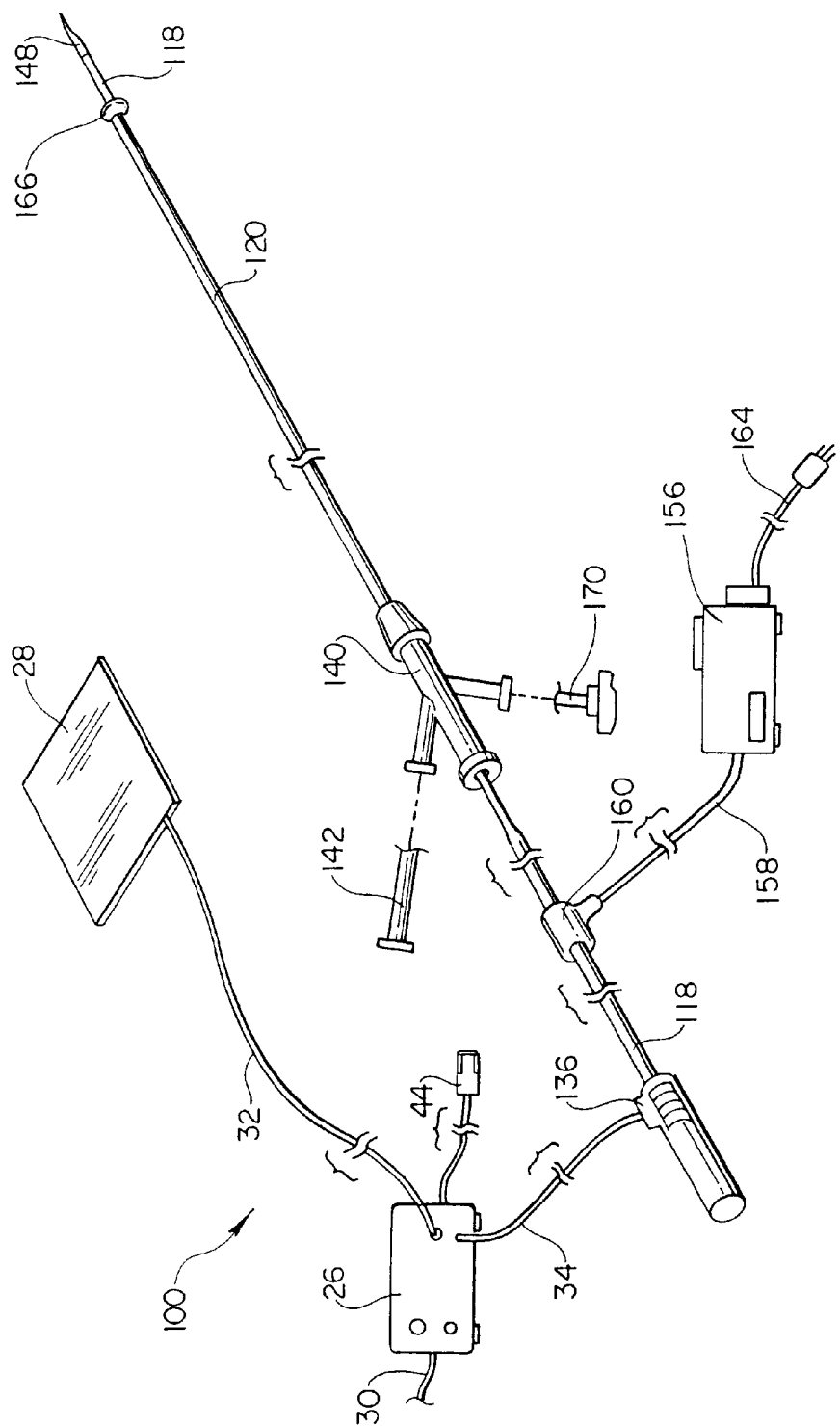
FIG. 2 is a diagram of the RF transmyocardial revascularization assembly including RF generator ground plane and catheter.

FIG. 2 is an embodiment 100 of the RF TMR catheter assembly in accordance with the present invention. Embodiment 100 includes an RF activated catheter 118 electrically connected at its proximal end near handle 136 to RF generator 26 by cable 34. Disposed at the distal end of catheter 118 is a cutting tip 148. A vacuum generator 156 is fluidly connected by tube 158 to catheter 118 at a tee 160, which is in turn is in fluid communication with distal tip 148 by way of a lumen (FIG. 3) 162 extending through catheter 118. Vacuum generator 156 is connected to a power source by way of cable 164 to remove tissue to avoid embolizing or to take a specimen.

Catheter 118 as shown in FIG. 2 is disposed through a tubular catheter 120 having a balloon 166 disposed at its distal end. Disposed at the proximal end of catheter 120 is an adaptor 140 having a side arm 142 in fluid communication with a central lumen 168 (FIG. 3) extending through catheter 120. A second side branch 170 of adaptor 140 is in fluid communication with an inflation lumen 172 (FIG. 3) extending through catheter 120 to balloon 166.

Figure 3:
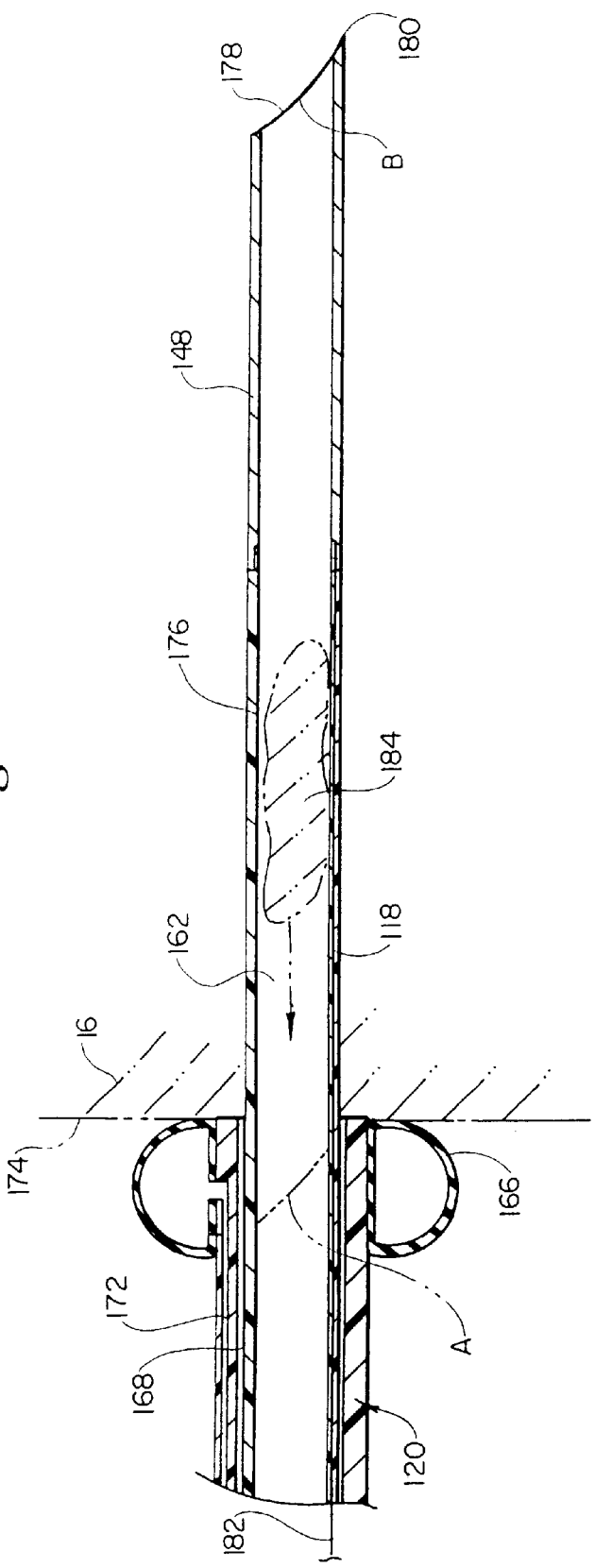
FIG. 3 is a cross sectional view of the distal end of the catheter apparatus of FIG. 2.

FIG. 3 is a cross sectional view of the distal ends of catheters 118 and 120. In this view, the distal end of catheter 120 abuts a heart wall 174 of heart 16. Distal cutting tip 148 of RF activated catheter 118 is shown extended into wall 174. Balloon 166 is shown inflated to shield pooled blood from RF energy. Catheter 120 and balloon 166 can be formed from typical guide catheter and angioplasty balloon materials, respectively, as well known to those skilled in the art.

Catheter 118 preferably includes a shaft portion 176 defining a portion of lumen 162 extending proximally from cutting tip 148, tip 148 defines the distal-most portion of lumen 162. Shaft 176 is readily formed from a biocompatible polymer well known to those skilled in the art of catheter construction having sufficient rigidity to allow cutting tip 148 to be pushed into heart wall 174.

Cutting tip 148 preferably has a sharpened distal edge 178 surrounding the distal opening of lumen 162. Tip 148 can include a sharp point 180 similar to that of hypodermic needle. The cutting tip 148 is preferably formed from stainless steel or other biocompatible metal. The proximal end of tip 148 is bonded or adhered to the distal end of shaft 176 in a manner known to those skilled in the art. The length of tip 148 varies according to channel requirement. In an exemplary embodiment, the outside diameter of cutting tip 148 is one millimeter and the inside diameter is 0.9 millimeters, but may vary depending on channel width desired. An RF transmission wire 182 connects cutting tip 148 to the proximal end of catheter 118 for interconnection with the RF generator 26.

In use, the cutting tip 148 of catheter 118 and the distal end of catheter 120 are advanced to the patient's heart 16, the hybernatory tissue to be cut having previously been identified by means known to those skilled in the art. Typically, hibernating tissue can be identified by injecting contrast medium into coronary vessels to identify regions of the heart into which the contrast medium does not flow due to obstruction of the vessels into which the medium is injected. In this case, the hibernating region will be identified by the lack of flow or abnormally low flow distally of the obstruction in the coronary vessel or vessels. Alternatively, the contrast medium can be injected directly into the heart chambers to identify areas within the chamber or chambers which have generally stagnant, pooled blood. If contrast medium has been injected into the coronary vessels, those regions of the heart into which the contrast medium does not flow, would be candidates for the RF TMR procedure. If contrast medium is injected directly into the heart chambers, the regions of the heart adjacent to the generally stagnant pooled blood would be candidates for the RF TMR procedure.

Access to the patient's heart will generally be obtained percutaneously through aorta 12 and ventricle 14. Balloon 166 can be inflated to help shield pooled blood within the ventricle from RF energy. As shown in FIG. 5, catheter 118 is advanced from a position A into the myocardium of the patient's heart at position B.

RF generator 26 is activated to emit RF energy from cutting tip 148. As cutting tip 148 is advanced into the myocardium, the RF energy loosens the material within lumen 162 from the heart. A plug of tissue 184 can then be aspirated through lumen 162 by vacuum generator 156.

The diameter of cutting tip 148 can be varied to vary the diameter of the channel formed by this procedure. Additionally, the RF output of RF generator can be varied by increasing pulse duration of the application of RF or the power of the RF radiation to speed tissue removal.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A radio frequency activated catheter assembly, comprising:

a first catheter including an elongate shaft having a proximal end and distal end, a lumen extending therethrough between the proximal and distal ends, and a cutting tip having a proximal end and a distal end, and a lumen extending therebetween in fluid communication with the shaft lumen;

a radio frequency generator;

a means for connecting the cutting tip to the radio frequency generator;

a vacuum source connected to the first catheter proximate the proximal end of the first catheter and in fluid communication with the first catheter lumens; and a second catheter including a proximal end, a distal end, a longitudinal axis extending therebetween, and a lumen extending therebetween, a balloon disposed at the distal end, an inflation lumen extending between the proximal and distal ends and being in fluid communication with the balloon, wherein the first catheter is disposed at least partially within the lumen of the second catheter, wherein the second catheter lumen terminates in a plane generally perpendicular to the second catheters longitudinal axis.

2. A radio frequency activated catheter assembly in accordance with claim 1, wherein the cutting tip is metallic.

3. A radio frequency activated catheter assembly in accordance with claim 2, wherein the distal end of the cutting tip is sharpened.

4. A radio frequency activated catheter assembly in accordance with claim 1, wherein the means for connecting includes wire.

* * * * *